US00PP09587P

United States Patent [19]

Guillou et al.

[11] Patent Number: Plant 9,587

[45] Date of Patent: Jun. 18, 1996

[54] GERANIUM PLANT NAMED GUIBER

[75] Inventors: Jacques Guillou; Bernard Guillou; Maurice Guillou, all of Saint-Malo, France

[73] Assignee: ETS. Guillou Freres, Saint-Malo, France

[21] Appl. No.: 384,529

[22] Filed: Feb. 1, 1995

[51] Int. Cl.[6] ..... A01H 5/00

[52] U.S. Cl. ..... Plt./87.12

[58] Field of Search ..... Plt./87.12

*Primary Examiner*—James R. Feyrer

*Attorney, Agent, or Firm*—Foley & Lardner

[57] ABSTRACT

A new and distinct cultivar of geranium plant named 'Guiber', characterized by its dark-carmine flower color, strongly double-type flowers, medium-green foliage, absent to very weak zonation which forms a ring near the base of the leaf, compact and good branching plant habit.

1 Drawing Sheet

The present invention comprises a new and distinct cultivar of geranium, botanically known as *Pelargonium, peltatum l'Hert,* and hereinafter referred to by the cultivar name 'Guiber'.

'Guiber' is a product of a planned breeding program which had the objective of creating new geranium cultivars with dark-carmine flower color and a compact and well-branched growth habit.

'Guiber' was originated from a hybridization made in a controlled breeding program in Saint Malo, Bretagne, France in 1985.

The female and male parents were unnamed hybrids from the proprietary Guillou collection, both parents having red double-type flowers.

'Guiber' was discovered and selected as one flowering plant within the progeny of the stated cross by the inventors in 1986 in a controlled environment in Saint Malo, Bretagne, France.

The first act of asexual reproduction of 'Guiber' was accomplished when vegetative cuttings were taken from the initial selection in 1986 in a controlled environment in Saint Malo, France by a technician working under the supervision of the inventors. Horticultural examination of selected units initiated in Jul. 1990 in Haalderen, The Netherlands, has demonstrated that the combination of characteristics as herein disclosed for 'Guiber' are firmly fixed and are retained through successive generations of asexual reproduction.

'Guiber' has not been observed under all possible environmental conditions. The phenotype may vary with variations in environment such as temperature, light intensity, and daylength without any charge in the genotype of the cultivar. The following observations, measurements, and comparisions describe plants grown in Haalderen, Holland under greenhouse conditions which approximate those generally used in commercial practice.

The following traits have been repeatedly observed and are determined to be basic characteristics of 'Guiber' which, in combination, distinguish this geranium as a new and distinct cultivar:

1. Dark-carmine flower color.
2. Double flowers.
3. Very medium-green foliage.
4. Absent to weak zonation which forms a ring near the base of the leaf.
5. Compact plant habit.
6. Good branching habit.

Of the many commercial cultivars known to the present inventors, 'Guiber' can be most closely compared to 'Guimauve.' 'Guimauve' does not produce pedicels that are light-red in the middle third. 'Guiber' has no markings on the upper petals while 'Guimauve' produces upper petals with markings.

The accompanying color photographic drawings show typical flower and foliage characteristics of 'Guiber'.

Figure 3:
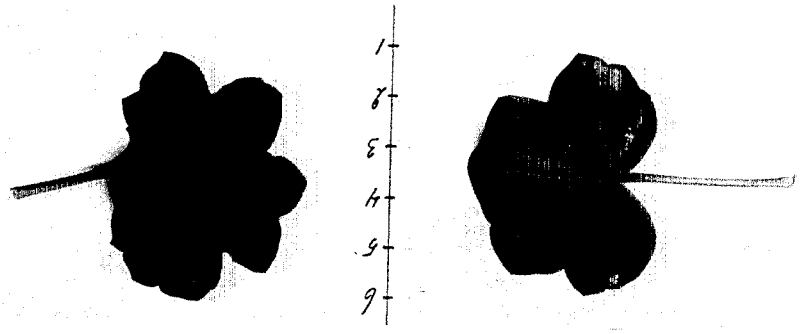
FIG. 3 is a top and bottom view of an individual leaf from the cultivar.
Figure 2:
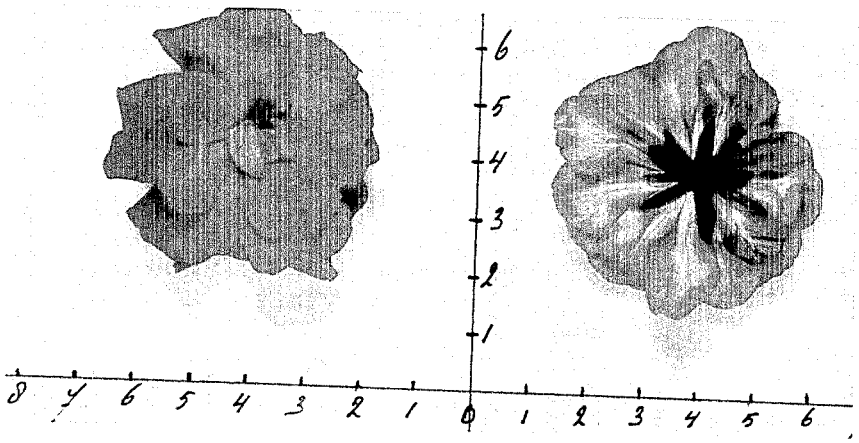
FIG. 2 is a top and bottom view of an individual flower from Guiber.
Figure 1:
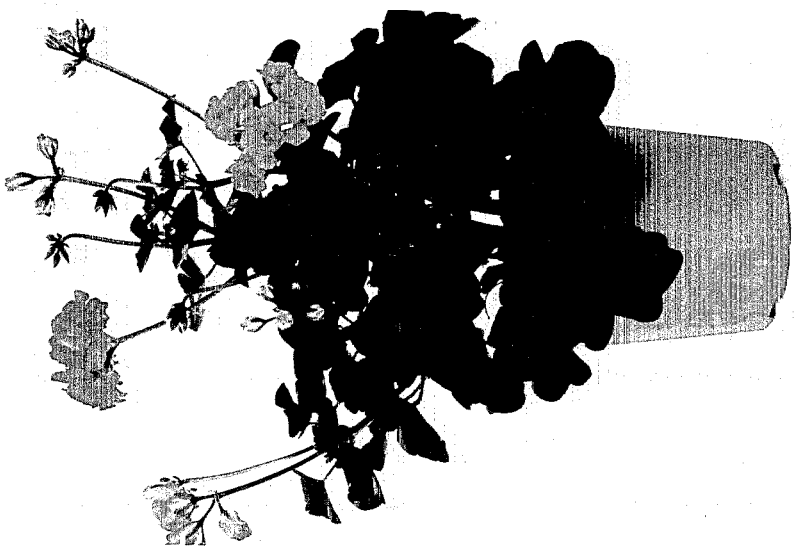
FIG. 1 is a side view of the cultivar.

In the following description, color references are made to The Royal Horticultural Society (R.H.S.) Colour Chart. The color values were determined indoors in 1991 under greenhouse conditions in Hannover, Germany with colors being as true as possible with illustrations of this type.

Classification:

*Botanical.*—*Pelargonium Peltatum l'hert* cv. 'Guiber'.

*Commercial.*—Ivy geranium, 'Guiber'.

INFLORESCENCE:

A. Umbel: Nearly semi-spherical with 6 to 8 buds per umbel.
- *Average diameter.*—95 mm.
- *Average depth.*—35 mm.
- *Peduncle length.*—95 mm.
- *Pedicel length.*—15 mm.
- *Pedicel color.*—Light-red in middle third.

B. Corolla:
- *Average diameter.*—45 mm.
- *Form.*—Strong double-type with 20 to 30 petals. The number of petals increases in the spring.
- *Color upper surface (General tonality from a distance of three meters).*—Red.
- *Color upper surface (abaxial).*—Dark-carmine (R.H.S. 52A).
- *Color upper surface (adaxial.*—Dark-red (R.H.S. 46C).
- *Color lower surface.*—Dark red margin with white center and white base.
- *Petal margins.*—Entire.
- *Petal size.*—Approximately 18–20 mm wide and 27 mm long.
- *Sepal number.*—5.

C. Bud:
- *Shape.*—Elliptic.
- *Color (abaxial).*—Green, no anthocyanin.
- *Color (adaxial).*—Dark-carmine, R.H.S. ca. 52a.

D. Reproductive organs:
*Androecium.*—3–7 fertile anthers, white filaments.
*Gynoecium.*—5–6 lobed stigma, red style stigma.

E. Spring flowering response period: 1.6 flowers opened 15 weeks after planting of unrooted cuttings (pinched plants).

F. Outdoor flower production: 80–90 umbels per plant from late April–May through September. Pinching of spent blooms is necessary to ensure continued flowering.

G. Durability: Shatter resistance is good.

PLANT

A. Foliage:
*Form.*—Ivy-shaped.
*Base.*—Open.
*Color (abaxial).*—Medium-green (R.H.S. 139A).
*Color (Adaxial).*—Green.
*Color (zonation).*—Green, absent to very weak.
*Variegation.*—Absent.
*Margin.*—Medium undulation.

B. General appearance and form:
*Internode length.*—30 to 40 mm,
*Branching pattern.*—5–6 branches per plant that are somewhat erect in growth habit.
*Height.*—50 to 55 cm in August.
*Plant vigor.*—Strong, vigorous growth that continues during the flowering period.

C. Tolerance to botrytis: Good.

I claim:

1. A new and distinct cultivar of geranium plant named 'Guiber', as illustrated and described.

* * * * *